United States Patent
Hellhund et al.

(10) Patent No.: US 12,191,028 B2
(45) Date of Patent: Jan. 7, 2025

(54) SAFEGUARDING MECHANISMS FOR THE OPERATION OF MEDICAL APPARATUSES USING DISPOSABLES IN A DIALYSIS ENVIRONMENT

(71) Applicants: Fresenius Medical Care Deutschland GmbH, Bad Homburg (DE); Fresenius Medical Care AG & Co. KGaA, Bad Homburg (DE)

(72) Inventors: Jonas Hellhund, Frankfurt (DE); Robert Lindemann, Wiesbaden (DE); Arne Peters, Bad Homburg (DE); Gerome Fischer, Weberstedt (DE)

(73) Assignees: Fresenius Medical Care Deutschland GmbH, Bad Homburg (DE); Fresenius Medical Care AG & Co. KGaA, Bad Homburg (DE)

( * ) Notice: Subject to any disclaimer, the term of this patent is extended or adjusted under 35 U.S.C. 154(b) by 701 days.

(21) Appl. No.: 17/432,197

(22) PCT Filed: Feb. 19, 2020

(86) PCT No.: PCT/EP2020/054289
§ 371 (c)(1),
(2) Date: Aug. 19, 2021

(87) PCT Pub. No.: WO2020/169637
PCT Pub. Date: Aug. 27, 2020

(65) Prior Publication Data
US 2022/0189616 A1 Jun. 16, 2022

(30) Foreign Application Priority Data
Feb. 20, 2019 (EP) .................................. 19158317

(51) Int. Cl.
*G16H 40/20* (2018.01)
*G06F 21/44* (2013.01)
(Continued)

(52) U.S. Cl.
CPC ............ *G16H 40/20* (2018.01); *G06F 21/44* (2013.01); *G16H 20/40* (2018.01); *G06F 21/64* (2013.01)

(58) Field of Classification Search
CPC ........ G16H 40/20; G16H 20/40; G06F 21/44; G06F 21/64
See application file for complete search history.

(56) References Cited

U.S. PATENT DOCUMENTS 10,984,081 B2 * 4/2021 Goeringer ............... G06F 21/64
11,016,754 B2 * 5/2021 Samson .................. H04W 4/80
(Continued)

FOREIGN PATENT DOCUMENTS

WO 2015/024647 A2 2/2015

OTHER PUBLICATIONS

Alblooshi et al., "Blockchain-based Ownership Management for Medical IoT (MIoT) Devices," 2018 International Conference on Innovations in Information Technology (IIT), IEEE, Nov. 2018, 151-156.
(Continued)

*Primary Examiner* — Jerry B Dennison
(74) *Attorney, Agent, or Firm* — Fish & Richardson P.C.

(57) ABSTRACT

The disclosure relates to a safeguarding module, a method, and a system for safeguarding an apparatus in the medical environment against an unauthorised operation of the apparatus, wherein the authorisation is dependent upon a linking event between two linking partners within the framework of an operation of the apparatus, wherein the apparatuses are connected via a network, and wherein one of the linking (Continued)

partners is an item which is used during the operation of the apparatus. The system comprises a plurality of apparatuses, wherein in each case an apparatus comprises a safeguarding module, comprising:
- a read-in interface for reading-in a first identifier and a second identifier;
- a processing unit which is designed to perform the safeguarding method;
- a memory for storing the calculated documentation value in a distributed ledger structure; and
- an interface to the network, via which the apparatuses exchange data.

18 Claims, 4 Drawing Sheets

(51) Int. Cl.
*G16H 20/40* (2018.01)
*G06F 21/64* (2013.01)

(56) References Cited

U.S. PATENT DOCUMENTS

| | | | |
|---|---|---|---|
| 2005/0194317 A1* | 9/2005 | Ikeyama | B01D 61/12 210/321.74 |
| 2007/0209977 A1* | 9/2007 | Wilf | B01D 61/025 374/45 |
| 2008/0296208 A1* | 12/2008 | Ikeyama | C02F 1/441 210/93 |
| 2016/0199559 A1 | 7/2016 | Glaser | |
| 2017/0046526 A1* | 2/2017 | Chan | G06Q 20/3829 |
| 2017/0295157 A1* | 10/2017 | Chavez | H04L 9/3239 |
| 2017/0300627 A1* | 10/2017 | Giordano | G06F 21/6245 |
| 2018/0096121 A1* | 4/2018 | Goeringer | G06F 21/316 |
| 2018/0096347 A1* | 4/2018 | Goeringer | G06Q 20/389 |
| 2019/0096522 A1* | 3/2019 | Scriber | H04L 9/3247 |
| 2022/0184186 A1* | 6/2022 | Andersen | A61K 38/465 |
| 2023/0261885 A1* | 8/2023 | Claypool | H04L 9/3239 713/193 |

OTHER PUBLICATIONS

Cachin et al., "Blockchain Consensus Protocols in the Wild," https://arxiv.org/abs/1707.01873, Jul. 2017, 1-24.
Distributed Systems: Principles and Paradigms, 2nd ed., Tanenbaum et al., 2007, Chapter 7.5, 306-317, 27 pages.
Extended European Search Report in European Appln. No. 19158317.8, dated Aug. 14, 2019, 26 pages (with machine translation).
International Search Report and Written Opinion in International Appln. No. PCT/EP2020/054289, mailed Apr. 24, 2020, 28 pages (with English translation).

* cited by examiner

SAFEGUARDING MECHANISMS FOR THE OPERATION OF MEDICAL APPARATUSES USING DISPOSABLES IN A DIALYSIS ENVIRONMENT

CROSS-REFERENCE TO RELATED APPLICATIONS

The present application is the national stage entry of International Patent Application No PCT/EP2020/054289, filed on Feb. 19, 2020, and claims priority to application Ser. No. 19/158,317.8, filed in the European Patent Office on Feb. 20, 2019, the disclosures of which are expressly incorporated herein in their entireties by reference thereto.

TECHNICAL FIELD

The present disclosure resides in the field of medical technology and relates to the operation of medical apparatuses, such as dialysis apparatuses and reverse osmosis units which are operated with disposables (e.g., single-use articles). The disclosure relates to methods for safeguarding an apparatus against an unauthorised operation, computer programs, safeguarding modules, medical apparatuses and systems.

In this respect, a specific feature concerning the operation of medical apparatuses in comparison with other non-medical operating methods is that the operation of the apparatus affects the health of a patient. In this respect, particular security measures are to be observed. Some operating methods provide for the use of disposables (such as, e.g., a dialyser). For example, in the case of haemodialysis, a dialysis treatment is typically performed on a dialysis apparatus, which can be located, e.g., at a dialysis centre, such that a patient registers at the dialysis apparatus in order to perform the dialysis. During the dialysis, the patient's blood is guided through an extracorporeal circuit which can be designed, e.g., as a single-use article. For this purpose, a set of disposables (e.g., a tube kit with tube lines, filter modules, connectors, drip chambers, etc.) which are carried along by the patient or are provided for the patient can be used.

For the treatment itself, the patient can use different dialysis apparatuses which are located in the same or even in different dialysis centres (sometimes distributed worldwide). From a medical perspective, it is important to ensure that the set of disposables is used in the designated manner. Specific applications require, e.g., that the set of disposables are only allowed to be used once, whereas other applications permit a limited number of re-uses. However, in any event it is necessary to ensure that the set of disposables is used only for precisely one patient (hence, said set must not be "lent" to fellow patients). However, a use on different machines can be allowed.

PRIOR ART

In the case of known systems from the prior art, the authorisation of a use of disposables was hitherto verified to an inadequate extent. This was generally performed manually by the treatment personnel, e.g., by manually checking with the patient. It is obvious that such a method is associated with serious disadvantages in some cases. In some cases, the personnel could completely forget to perform the verification and therefore this would not be carried out, and in other cases the information sources may not be reliable. This adversely affects the security of the operation of the apparatus and can have a disadvantageous effect upon the entire treatment process.

For example, it is known from WO2015024647A2 to provide the item of use with a sensor in order to be able to detect and process measurement values during the course of the treatment. The sensor can be, e.g., a fill-level sensor of a dialysate container as an example of an item of use or can be a temperature sensor for detecting the temperature.

Taking into consideration the practical situation during a dialysis treatment, the greatest possible flexibility for the patient is required. Occasionally, the patient should be able to be treated at any dialysis apparatus of any dialysis centre (e.g., distributed worldwide) using a set of disposables which he has brought along. Therefore, it is not adequate to verify the use of the disposables on a specific apparatus locally.

Moreover, it is important that the security of the data stored in relation to the patient, disposables, etc. satisfies the requirements of data protection, e.g., the protection of PHI data (private or protected health information), and the stored data cannot be reviewed by unauthorised persons.

Therefore, an aspect of the present invention is to provide a technical implementation, by means of which the security of an operation of the apparatus can be increased and the risk for the patient can be reduced, and in so doing to ensure or even increase further the flexibility for the operator or for the patient, e.g., to enable selecting any treatment apparatus. Furthermore, the traceability of an operation of the apparatus, e.g., treatments performed, is to be improved to allow conclusions to be drawn relating to respective apparatuses and to improve the documentation thereof. Furthermore, the technical implementation is to be efficient such that long waiting times by reason of verification measures on the apparatus can be avoided.

Therefore, a first aspect relates to a method for safeguarding an apparatus in the medical environment against an unauthorised operation of the apparatus, wherein the authorisation is dependent upon a linking event between two or more linking partners within or in the context of an operation of the apparatus, wherein the apparatus is connected at least intermittently to a network for exchanging data with other apparatuses and wherein one of the linking partners is an item of use which is used during the operation of the apparatus, comprising the methods steps of:

reading-in a first (digital) identifier which identifies a first linking partner in a unique manner and reading-in a second (digital) identifier which identifies a second linking partner in a unique manner. The reading-in procedure can be performed via a reading interface of the apparatus;

applying at least a first calculation rule to the read-in first identifier and applying a second calculation rule to the second identifier for calculating a documentation value which uniquely represents a linking event between the first and second linking partners; in order to calculate the documentation value a third calculation rule can be applied; the calculation is performed on a digital processing unit which can be part of a safeguarding module;

storing in a synchronised manner the calculated (and optionally: validated) documentation value in memories of a distributed memory structure of all or selected apparatuses of the network (preferably of a plurality of apparatuses).

It is ensured that the calculating rules are known by all of the participating apparatuses. Therefore, in an embodiment, a preparation phase is provided which serves to exchange the calculation rules used, comprising the first, second, and optionally third calculation rule, in order to enable the apparatuses to be able to write and read data to the distributed data structure.

A further aspect relates to a method for documenting in a tamper-proof manner an operation of the apparatus of a medical-technical apparatus which can be operated using an item of use (for a specific patient). For this purpose, a linking event is represented in digital form in a documentation value. The documentation value represents in a tamper-proof manner the use of a specific item of use (e.g., dialyser) for a specific patient on a specific apparatus (e.g., a dialysis apparatus) or the use of a specific item of use (e.g., membrane) on a specific apparatus (e.g., a reverse osmosis unit). The tamper-proof documenting is effected by storing the calculated documentation value. The method likewise includes the above-described method steps of reading-in, applying and storing in a synchronised manner.

The alternative embodiments set forth hereinafter can relate to both variants of the method.

In one advantageous development, the method can comprise a validation of the calculated documentation value on the part of a group of apparatuses in the network by applying a consensus algorithm so that the storing and/or authorising of the operation of the apparatus are performed only when the validation is successful.

In one advantageous development of the method, when the validation is successful, the method can include the authorising of the operation of the apparatus for (or with) the first and second linking partner, or the method can activate the apparatus. Otherwise, if the validation is not provided, the apparatus can be disabled, at least for the use with the respective linking partner.

The safeguarding method is effective, can be performed on distributed smart devices (e.g., IoT devices, IoT: Internet of Things) without the need for a central entity, and is also highly tamper-proof.

The validation of the calculated documentation value can be performed on a configurable group of apparatuses. The group is formed from a plurality of apparatuses. It can be configured such that essentially all of the apparatuses are used for the validation or only selected ones are used (e.g., ones having sufficient computing capacity).

The linking partners are formed having physical identification markings or are denoted by labels which can be used to identify them in a biunique manner. The identification markings can be formed, e.g., as a code (e.g., as a bar code or QR code). This identification marking is allocated in a unique manner to an identifier or can be transformed into this by means of a mapping rule. The identifier must be provided and communicated in a suitable manner to an apparatus in the network to ensure that the safeguarding method can be carried out.

In one embodiment, the linking partner can be allocated to an electronic device (e.g., the patient's mobile phone/smartphone) which stores the respective digital representation or instance of the identification marking identifying the linking partner (e.g., patient ID in an app). This digital representation can then be communicated as a patient identifier to the apparatus for further processing.

In a further embodiment, an item of use can be provided with a physical identification marking (e.g., bar code or RFID chip). This identification marking can be read-in via a corresponding reading means (e.g., scanner, bar code scanner, or RFID reader) and transformed into a digital instance which henceforth functions as a digital identifier for the item of use. The reading means can be integrated into or allocated to the apparatus (e.g., dialysis apparatus). It is also possible to input an identifier, which identifies the respective linking partner, directly and manually (e.g., via a user interface) on the apparatus.

In another embodiment, the apparatus (e.g., dialysis apparatus or reverse osmosis unit) itself is designed having a safeguarding module for performing the method and having interfaces for reading-in the first and second identifier.

In a further embodiment, the apparatus itself is not designed having a safeguarding module but instead exchanges data therewith at least intermittently or in phases. The safeguarding module is then formed on another apparatus which functions as a gateway or intermediary. In this case, the term "gateway" is to be understood to mean an intermediary node and can be designed, e.g., as a smartphone, tablet, or other type of mobile terminal.

The linking partners transmit their identifier to an apparatus of the network via a preferably wireless network (e.g., radio, WLAN, optical etc.). The linking partner (e.g., the disposable) can transmit its physical identification marking, e.g., as a bar code to a reading means or reading-in device (e.g., bar code scanner) which converts the read-in code into a digital identifier and transmits it to the dialysis apparatus.

In this embodiment, two different networks can thus be implemented: A (first) network between the linking partners (e.g., disposable with RFID chip) and their allocated devices or reading means (e.g., RFID scanner) and another (second) network which serves to exchange data between the apparatuses, to which the safeguarding method is to be applied (e.g., in the dialysis apparatus or as a gateway) and their memories form a distributed data structure. The latter can be based in particular upon an IP protocol.

Terms used in application and advantageous embodiments are specified hereinafter.

An apparatus can be a medical apparatus (e.g., a dialysis apparatus) or a non-medical apparatus which is used in the medical environment (e.g., a reverse osmosis unit which is abbreviated hereinafter as RO unit) or an apparatus which is operated with an item of use during therapeutic apheresis. The medical apparatus can be, e.g., a haemodialysis apparatus, a haemodiafiltration apparatus, or a peritoneal dialysis apparatus. The dialysis apparatus is operated preferably in a cluster of apparatuses. For instance, the dialysis apparatus can be operated with others in parallel in a dialysis center. However, the dialysis apparatus can also be operated as a home dialysis apparatus. Different dialysis centers are operated worldwide.

A significant advantage of the proposed solution can be seen in the fact that the apparatuses originate from different manufacturers and/or can be operated by different operators in order to be able to take part in the safeguarding method.

The apparatus can also be a home haemodialysis apparatus. Specifically in this case, re-use of a dialyser is very advantageous for financial reasons. However, on the other hand, the patient is largely unsupervised by specialist medical personnel. In this case, the repetition or re-use number permissible for health reasons could easily be exceeded without being noticed (or even intended for cost reasons), so the safeguarding or verifying to ensure that excessive repetitions do not occur is extremely helpful. At the same time, it is desirable for health insurance funds and manufacturing companies to ensure that it is documented in a tamper-proof manner if an impermissible repetition number occurs. It is thus possible, where appropriate, to clarify liability rules and confirm compliance with treatment plans.

An item of use can be a disposable. The item of use can be designed as a single-use or multiple-use article for a dialysis apparatus, such as, e.g., a dialyser, a blood line, or a dialysate line which can be designed as tube lines. The item of use can likewise relate to a membrane or other item of use for a reverse osmosis unit. In a further example of use, the item of use can also be a dialysis filter such as a dialyser for haemodialysis and/or haemodiafiltration. In a further example of use, the item of use can also be an adsorber for a therapeutic apheresis. In advantageous embodiments, the item of use can also be another item or a further apparatus which is used or operated with the apparatus.

The authorisation is based upon an automatic verification of the permissibility to use an item of use for the medical-technical apparatus and/or for a patient. Depending upon use, different permissibility requirements can be configured, such as, e.g., only one-time use or multiple use of the item of use with a configurable limit of the number of permissible uses or other permissibility criteria (e.g., maximum service life, maximum operating time, etc.) for the respective linking partner (e.g., dialysis machine). The authorisation can include activating the apparatus and/or disabling it for the planned operation of the apparatus with the item of use. The authorisation can also include further permissibility checks (e.g., see above: the verification of permissibility requirements).

A first linking partner can be a patient who is being treated on a dialysis apparatus and a second linking partner can be an item of use (dialyser, tube kit for the extracorporeal blood circuit, etc.) for use with the dialysis apparatus. Alternatively, the first linking partner can be a reverse osmosis unit and the second linking partner can be a membrane or another item of use for the reverse osmosis unit. A linking partner can have an identification marking (e.g., in the form of a QR code) which identifies it in a unique manner. This identification marking is allocated in a unique manner to a digital identifier. For example, each patient has a patient identifier which identifies him, and each item of use has a disposable-identifier which identifies it.

The apparatuses can be communication partners in a network which can exchange data via a preferably wireless network (e.g. WLAN, according to a protocol as per the standard IEEE-802.11 family) and can write and read data to a distributed memory structure.

The first and second identifiers serve in each case to identify the first and second linking partners, respectively, in a unique manner. The identifier is preferably a digital or electronically processable identification code which is allocated bijectively to an identification marking applied directly on the linking partner (e.g., item of use is marked) or is allocated thereto (e.g., a patient has a patient card identifying him). The identifier can be generated, e.g., via a random generator and can be processed with an algorithm so as to ensure that a unique allocation is guaranteed between the identifier and linking partner so that precisely one identifier is allocated to precisely one linking partner.

The identification marking is a physical label, tag, or token and can be applied directly on the item of use, e.g., as a stuck-on electronic label. An identification marking can include, e.g., numbers, letters, special characters, and combinations thereof. The identification marking can also be allocated in a unique manner to a linking partner. The identification marking is detected or read-in via corresponding interfaces or reading-in means (e.g., data interface, optical sensor, or scanner). The identification marking can be an identifier which serves to uniquely identify the linking partner (e.g., bar code, QR code) and can be electronically detected and evaluated. If the identification marking is read-in, then it can be allocated to an identifier by means of a unique mapping rule.

A linking event represents the linking of at least two linking partners. In this case, the term "linking" means a common operation or the use of an item of use by a consumer at the time of or during an operation. The apparatus can assist in the linking event. The linking event can occur during set-up, preparation, commissioning and/or during operation of the apparatus. In other words, the linking represents, e.g., the use of a specific dialyser or tube kit as an item of use in the dialysis apparatus for the specific patient or the use of the specific membrane in the reverse osmosis unit. Initially, a linking event is intended or requested by at least one of the linking partners. This can be triggered, e.g., by the patient introducing his ID card into a receiving device on the apparatus and/or inputting corresponding user inputs on a user interface and/or by an identifier of the item of use to be used being read-in. In order to increase security, the linking event is documented and stored at least in a tamper-proof and retrievable manner. Furthermore, provision can be made that the linking is not implemented forthwith but instead that initially a verification is performed to establish whether the planned use is also authorised. To this end, the distributed memory structure is accessed with a defined access algorithm. A linking event can be detected on the basis of configurable criteria. The linking event can be detected in a time-based manner (e.g., in a timed manner or after a specific number of uses) or in an event based manner (e.g., after engagement or performance of a specific action). The detection of a linking event can include the validation. However, it can also be the case that the detection includes the reading-in, application, and validation. In other words, these method steps are only performed if a trigger criterion is met (time-based, event-based). In one embodiment, the identifiers can be read-in and the calculation rules can be applied.

The first, second, third and/or further calculation rule and/or the linking function can be a rule which is to be performed on a digital computing unit. In an embodiment of the invention, these calculation rules are identical. In a simple embodiment, the two identifiers are hashed together and the value is thereby generated. In this simple case, no further operation is performed. In this case, an identifier is used as a seed for a hash of the respective other identifier.

However, the calculation rules, e.g., the first and the second calculation rules, can also be different. The first calculation rule is applied to the first identifier in order to calculate a first partial result and the second calculation rule is applied to the second identifier in order to calculate the second partial result. The linking function is used for calculating the documentation value from the first and second partial results. For example, the calculation rule and/or the linking function can be cryptological. The calculation rule and/or the linking function can be, e.g., a cryptological hash function or a simple hash function, such as the use of an SHA, MD5 or other algorithm.

The documentation value is calculated from the first partial result (i.e., application of the first calculation rule to the first identifier) and from the second partial result (i.e., application of the second calculation rule to the second identifier). The third calculation rule can be applied to the first and second partial result in order to calculate the documentation value. Furthermore, in alternative embodiments the documentation value can comprise further data, e.g., measurement data accumulating during the use of the apparatus with the linking partners (e.g., with the respective disposable during a dialysis treatment). Further data which are securely documented with the method can be:

apparatuses ID, components IDs, location data, treatment data such as average blood pressure, clearance, average conductivity of the dialysate (e.g., Na concentration), etc.

information relating to the communication connection (e.g., latency, IP address, Mac address, physical location). The tracking of this data has the technical advantage that the quality of the communication connection can be predicted and/or the system can thus be designed on the whole in a more reliable manner.

period of performance of the method on this apparatus. The period of performance can be different for different hardware. The advantage is founded in improved predictability.

the aforementioned list of further data can be extended. Basically, all treatment and environment data are feasible, such as, e.g., blood pressure and administration of medication such as heparin, Epo, etc. Moreover, alarms can be part of the further data.

The network is a network for exchanging digital data for performing the safeguarding method. The network can be designed as a peer-to-peer network and offers the communication participants the possibility of taking advantage of services and resources of other communication participants with equal rights. The network is open to all network participants. This does not represent a security risk because the data stored in the distributed memory structure are stored in a secured manner and are encrypted in a cryptological manner and therefore are not provided in clear text even during monitoring.

In this case, a "program" or "program instructions" is/are understood to mean every type of computer program which comprises machine-readable instructions for controlling a functionality of the computer. The computer program can be stored on a data carrier as an executable program file, frequently in the so-called machine code, which is loaded in the working memory of the computer for execution. The program is processed and thus executed as a sequence of machine commands, i.e., processor commands, by the processor(s) of the computer. The program can be provided as an executable code, as a source code or as an interpreted code.

An "interface" is understood to be an interface, via which data can be received and transmitted (i.e., a communication interface). The communication interface can be configured to be a contact interface or contactless interface. The communication interface can be an internal interface or an external interface which is connected to an allocated apparatus, e.g., means of a cable or wirelessly. The communication can be effected via a network. In this case, a "network" is understood to be every transmission medium having a connection for communication, e.g., a local connection or a local network, a local area network (LAN), a private network, an Intranet, or a virtual private network (VPN). For example, a computer system can have a standard radio interface for connection to a WLAN. Furthermore, it can be a public network, such as, e.g., the Internet. Depending upon the embodiment, the communication can also be effected via a mobile network.

In this case, a "memory" is understood to be either volatile and non-volatile electronic memories or digital memory media. A "non-volatile memory" is understood to be an electronic memory for the permanent storage of data. A non-volatile memory can be configured as a non-alterable memory which is also defined as a read-only memory (ROM), or can be configured as an alterable memory which is also defined as a non-volatile memory (NVM). For example, it can be an EEPROM, e.g., a flash EEPROM, or flash for short. A non-volatile memory is characterised in that the data stored therein are also retained even after the power supply is switched off. In this case, a "volatile electronic memory" is understood to be a memory for temporarily storing data, which is characterised in that all of the data are lost after the power supply is switched off. For example, this can be a volatile direct access memory which is also defined as a random-access memory (RAM), or a volatile working memory of the processor.

A "processing unit" is understood to be an electronic module. This is typically a digital processing unit which can be implemented as a software module, e.g., as part of virtual machines. The processing unit can be designed, e.g., as a processor for the computer-based, automatic execution of commands and can comprise a logic circuit for executing program instructions. The logic circuit can be implemented on one or more discrete devices, e.g., on a chip. A "processor" is understood to be a microprocessor or a microprocessor system consisting of a plurality of processor cores and/or a plurality of microprocessors.

The statements provided above in relation to the processing unit equally apply accordingly to the safeguarding module also. This can also be designed as a software module, e.g., as part of a virtual machine.

In another embodiment, the documentation value can additionally provide further information relating to the respective linking event which permit, e.g., a statement as to whether the set-up of the dialysis machine is sufficient and adapted to be able to be brought into engagement with the respective parts of the extracorporeal circuit. Furthermore, the documentation value can provide still further meta data relating to the linking event (point in time, duration, number of previous uses, optionally repetition rate, number of remaining uses, etc.).

A consensus algorithm is executed distributed on a plurality of nodes or apparatuses and serves to establish a consensus or an agreement in relation to a value and thus to validate the value. It is executed uniformly on all or selected ones of the apparatuses or participants of the documentation method in order to provide a corresponding basis for evaluation. The consensus algorithm is operated according to a consensus protocol and can be designed as a proof-of-work or (delegated) proof-of-stake algorithm. A consensus algorithm relates fundamentally to a mechanism for achieving a uniform agreement (consensus) over the status of the decentralised network. A consensus algorithm facilitates the verification and validation of information which are written to (stored in) the distributed data structure (DL, distributed ledger). This ensures that only authentic data are recorded in the distributed data structure. The rules for use in the consensus protocol are hard-coded, agreed mutually amongst all participants and represent the single source of verification rules such that it is possible to ensure that the stored information is reliable without a central entity being required. For further details, reference is made to the following paper "Blockchain consensus protocols in the wild", C Cachin, M Vukolić—arXiv preprint arXiv:1707.01873, 2017—arxiv.org (v2). Only when a documentation value could be validated can it be stored in a synchronised manner in all memories of the linking partners which form a distributed memory structure. The consensus algorithm includes an access to the distributed memory structure. The validation by means of the consensus algorithm is used for searching locally whether the respective value has already been stored once, and if so, how often. In one extension, still further steps can be performed, such as, e.g., the application of rules made available in a rule base and/or computer-implemented algorithms based thereon. The validation is effected in a similar manner to the classic blockchain, in that a participant in the network (gateway or apparatus) attempts to verify a calculated value (corresponding, e.g., to a transaction with Bitcoin) by attempting to generate the same (identical) signature. The search in the distributed ledger can be effected directly after the signature and is thus more rapid in comparison with a search via memory addresses, block names, etc.

It can be configured such that an operation of the apparatus can only be activated when it has been evaluated to be authorised with the respective linking partners. For the evaluation, a successful validation (as explained above on the basis of the calculated documentation value) is a compulsory requirement. In order to authorise the apparatus, it is possible under certain circumstances to perform still further checks (time-based, event-based, etc.). Therefore, the operation of the apparatus can be safeguarded in a flexible and distributed manner against an unauthorised operation.

Synchronised storage means that a documentation value, insofar as it could be successfully validated, is stored in an identical manner in all of the memories of the apparatuses of the safeguarding method or safeguarding system. The apparatuses can be, e.g., a group of dialysis apparatuses and/or a reverse osmosis unit. The apparatuses of the validation method do not necessarily have to correspond with the linking partners. Therefore, the core step for safeguarding the operation of the apparatus, namely the validation, cannot be performed directly on the linking partners but instead on other computer-based nodes or entities, e.g., on gateways or nodes allocated to the apparatuses. All of the memories of the apparatuses are always in the same state and have the same memory status. This produces a distributed memory structure.

The distributed memory structure is preferably a distributed ledger structure (DLT structure) which can be implemented on all potential apparatuses and participants of the safeguarding method. To this end, the apparatuses are equipped with means (including memory means and software means) in order to participate in the distributed ledger structure. A distributed ledger system can store data which refer to different transactions or calculations between or by a plurality of computing apparatuses (e.g., a plurality of dialysis apparatuses). The distributed ledger system can be designed as a blockchain ledger system which comprises a multiplicity of "blocks" which each constitute one or more discrete transactions which take place between the computing apparatuses. Each block can comprise data which can be linked to a previously generated block, thus producing a complete chain between the generation of data, which are stored in the distributed ledger, and the later use of the same data (e.g., for establishing a complete chain of uses of disposables for a patient in an apparatus). The data stored in the different transactions/blocks can be encrypted, provided with a password, or otherwise protected against unauthorised access (e.g., read access, write access, and/or delete access). In a non-limiting example, information stored in the different blocks can be irreversibly hashed such that the hashed data can be used in order to verify the authenticity of transactions, ensuring that the hashed data cannot be retrogressively developed in order to ascertain substantial information based solely on the hashed information. Therefore, security-critical medical data can be distributed in a secure manner. Furthermore, data transmitted between different computers can be encrypted (e.g., by using public/private key pairs for digital signing and/or verifying data) and so blocks stored within the block chain can be verified by a plurality of apparatuses which have access to the public and/or private keys. After verifying (validating) the data to be stored in the blockchain, the data can be hashed and stored as described above. For further details relating to the concepts of distributed system/distributed ledger, reference is made to A. S. Tanenbaum, M. van Steen: Verteilte Systeme [distributed systems], 2007, in particular chapter 7.5. Processes for performing the documentation method run on the individual distributed computing entities or computers. Processes on the different computing entities in the distributed system communicate with one another by sending messages. In so doing, the processes must observe rules, e.g., in relation to the formats, the meanings of the exchanged messages, and the required actions for communication. These rules are defined as a protocol.

The safeguarding method produces blocks (data blocks) in a multiplicity of chains (in contrast to a blockchain, where typically there is precisely one chain). The blocks of the chain form a data collection. The distributed memory structure can be designed as a modified blockchain structure. The modification relates to the fact that a data block according to a basic embodiment consists merely of the calculated documentation value (hash value) which represents a unique signature. A data block does not have to contain a reference to the other blocks of the chain. In contrast to the classic blockchain, in order to compute a data block it is not necessary to access a mining pool. The calculations can be performed considerably more quickly and also on less powerful computer units and are still stored in a tamper-proof manner. A further structural difference with respect to the architecture of the blockchain is that the modified blockchain structure comprises a plurality of chains and therefore constitutes a multi-chain dataspace. In a first embodiment, a chain can relate in each case to a linking partner, e.g., a patient or a reverse osmosis unit. A plurality of chains (e.g., one chain for each item of use or for each patient) can be stored in a distributed memory structure (e.g., on a group of dialysis apparatuses). Since a patient generally does not change his identifier but uses many consumables (which each have individual identifiers), many chains should be produced for each patient—but only one for each item of use.

In an embodiment, a dialysis apparatus has a memory or memory region provided thereon, in which an instance of the distributed memory structure is stored (e.g., as a modified blockchain). All of the linking events which are performed (i.e., validated) and/or intended (not yet validated) on the dialysis apparatus can be stored at this location. The linking events can relate to different disposables and/or to different patients. This has the technical advantage that safeguarding can be performed locally on a participant (apparatus) by means of a validation check. For example, the validation check can advantageously also be performed when intermittently there is no (or no sufficient) communication connection to other apparatuses because the memories of the apparatuses are always synchronised.

In one embodiment, the calculation of the documentation value includes calculating a repetition value. The repetition value represents in a unique manner a repetition rate or a permissible number of repetitions for a linking event between the first and second linking partners.

Therefore, it can be securely documented in a comprehensive and differentiable manner whether, and if so how many, repetitions of linking events have already been detected. In a configuration phase, it is, e.g., possible to configure how many repetitions of a linking event are considered to be permissible. For instance, it may be allowed in some applications that a set of disposables for a specific patient may be used more than once by him. However, a configurable maximum number of repetitions may have been defined in order to restrict any use going beyond the maximum number. The major advantage can be seen in the fact that the distributed memory structure can ensure that the patient can use a disposable, which is initially linked to him/is uniquely allocated to him, with different dialysis machines.

In a further embodiment, the document value is calculated by applying an (e.g., cryptological) third calculation rule to a first partial result and a second partial result to provide a third partial result. The first partial result is calculated by applying the first calculation rule to the first identifier. The second partial result is calculated from applying the second calculation rule to the second identifier. In one advantageous variant, a further (mathematical) linking function can optionally be applied to the third partial result in order to calculate the total result. Otherwise, the third partial result can also function as the total result. When selecting suitable linking functions and/or calculation rules, the method and system cannot be corrupted or can only be corrupted by very long lasting, complex calculation methods.

In a further embodiment, if the validation is not successful the apparatus is disabled for the respective linking partners, at least for the intended use. This has the advantage that the apparatus can thus continue to be operated for other authorised linking partners. The disabling can be indicated by a warning notice which is output on a user interface. Therefore, the security of the operation of the apparatus can be increased. The automatic disabling of the apparatus can prevent and rule out errors resulting from the failure to perform a check manually.

In some embodiments, all of the apparatuses apply the same calculation rules for calculating the documentation value if they access the distributed memory structure.

According to one development, the validation and/or authorisation of the linking event can be performed in a timed manner and/or in an event-based manner. This has the technical background that for specific types of disposables it is necessary to monitor how long (e.g., in which time intervals) and/or in which quantity they have been used. This is important, e.g., when monitoring the use of an adsorber during a therapeutic apheresis. A linking event is detected according to a pre-configurable schedule (e.g., time schedule). This renders it possible to generate a clocking of linking events in order to make it possible to verify an operating time and/or service life and to store the same in a tamper-proof manner.

The solution has been described above by reference to the method. Features, advantages or alternative embodiments mentioned herein are also to be transferred to the other claimed subjects and vice versa. In other words, the apparatus claims (which are directed, e.g., to a system, an apparatus, or a safeguarding module) can comprise the features which are described and/or claimed in conjunction with the method and vice versa. In so doing, the corresponding functional features of the method are embodied by corresponding physical modules, e.g, by hardware modules or microprocessor modules of the system or of the product, and vice versa.

A further aspect relates to a computer program having program code which is suitable for executing the above-described safeguarding method if the computer program is executed on a computer, a computer-based processing unit, or a safeguarding module. The computer program can be stored in a memory and can be available, e.g., as an app on the dialysis apparatus and/or the reverse osmosis unit. However, it can also be implemented on a central computing unit which exchanges data (communication connection) with the respective apparatuses. The program can also be loaded via download by means of a network connection of a computer-based unit.

A further aspect relates to a safeguarding module for a medical apparatus, to which an application can be loaded and executed in order to perform the preceding method if the application is executed on a digital processing unit, e.g., on the safeguarding module. For this purpose, the safeguarding module comprises:

a read-in interface for reading-in a first and a second identifier;
an electronic processing unit which is designed to perform the safeguarding method as described above;
a memory for storing a calculated documentation value; alternatively, the memory can be swapped such that only one interface to the memory is integrated on the safeguarding module;
an interface to the network, via which the apparatuses exchange data.

This aspect is geared towards the achievement of the advantages; however, the above-described method is not performed directly on the apparatus (dialysis apparatus or reverse osmosis unit) but instead is performed on a separate digital computer-based unit, namely the safeguarding module which exchanges data with the apparatus and provides additional safeguarding through the performance of the method. Then—depending upon the result of the safeguarding method—the safeguarding module can transmit an enabling signal or disabling signal to the apparatus. The safeguarding module can be designed, e.g., as a mobile electronic terminal (tablet, smartphone, etc.). The safeguarding module can also be implemented on the dialysis apparatus or another apparatus. The safeguarding module can be provided as a software module and can be part of a virtual machine.

In one embodiment, a unit which comprises the safeguarding module or the safeguarding module itself has an interface to further safeguarding modules of other apparatuses of the network in order to form, on the whole with the respectively allocated memories, a distributed memory structure which can be designed, e.g., as a DLT structure.

A further aspect relates to a medical apparatus comprising a safeguarding module, as described above. In this case, the safeguarding module is implemented as a pure electronic processing unit without further functionality, such as, e.g., a microprocessor or an integrated circuit arrangement (FPGA etc.).

A further aspect relates to a system for safeguarding an apparatus in the medical environment against an unauthorised operation of the apparatus, wherein the authorisation is dependent upon a linking event between two linking partners as part of an operation of the apparatus, wherein all or selected ones of the linking partners are allocated in a unique manner to an identifier. One of the linking partners is an item of use which is used during the operation of the apparatus. An important aspect can be seen in the fact that the apparatus is operated in a distributed apparatus cluster and that one of these apparatuses of the apparatus cluster is to be safeguarded without a central control entity. For this purpose, each apparatus comprises a safeguarding module, as described above, which exchanges data with a distributed memory structure via the network.

In one embodiment, the memories of the apparatuses form a distributed data structure (e.g., a distributed ledger) which is continuously synchronised such that a local access to the memory of the local apparatus is sufficient for validating a documentation value. The synchronised data records are provided at least and primarily locally and are required with a certain minimum probability on this apparatus (within the clinical facility) if it is assumed that, in general, the patient visits the same clinic. Therefore, both the efficiency of the method can be increased and the required (network) resources can be protected. Records not provided locally can also be addressed via the network. For this purpose, slightly more time may be required for the validation for subsequent authorisation—depending on the available bandwidth. If the memory of an apparatus is limited such that only a part of the distributed ledger structure is to be stored locally, then the part held available locally can advantageously be selected so as to relate to the patients for whom the probability of being at this location once again for treatment is increased. An increased probability of being treated again at this location could be read, e.g., automatically from a data record that a patient has already been treated at this location. This provides the advantage that an authorisation method would be possible by comparison with the part of the ledger held available locally. This would, in turn, be quicker than possibly downloading ledger parts from remote and slowly coupled apparatuses. In variants in which each apparatus holds only a section of the ledger available, this variant of the method would be particularly advantageous.

In one embodiment, an identification marking of a first linking partner (e.g., medical disposable) can be an electronic processing unit (e.g., an RFID chip), wherein the electronic processing unit is arranged to store a unique disposable identification marking which, in turn, is allocated in a unique manner to a disposable identifier. A second linking partner can be a patient who wishes to perform a dialysis treatment with the disposable on an apparatus. The patient has a patient identification code which identifies him (e.g., the patient's ID card, a health card which he uses to register at the dialysis apparatus). The linking event represents the use of the respective disposable for the respective patient during a treatment on a specific medical apparatus.

In a further advantageous embodiment, a first linking partner is a membrane which is marked with an identification reference. The identification marking can be, e.g., in the form of an integrated or applied RFID chip which functions as an electronic processing unit. The identification marking can be read-in via suitable read-in means (e.g., a scanner) and is allocated in a unique manner to a membrane identifier (as a digital data record). A second linking partner is a reverse osmosis unit which can be identified likewise in a unique manner by means of a unit identifier. The linking event represents the use of the membrane in the reverse osmosis unit.

The advantages are further achieved by a computer program product, comprising computer program code, for performing all of the method steps of the method described in more detail above when the computer program is executed on a computer. In this connection, it is also possible for the computer program to be stored on a computer-readable medium. The computer program product can be designed, e.g., as a stored, executable file, optionally comprising further components (such as libraries, drivers, etc.) or as a computer comprising the already installed computer program.

BRIEF DESCRIPTION OF THE FIGURES

In the following detailed description of the figures, exemplified embodiments, which are to be understood to be non-limiting, together with the features and further advantages thereof will be discussed with the aid of the figures of the drawing. In the drawing.

DETAILED DESCRIPTION

Figure 1:
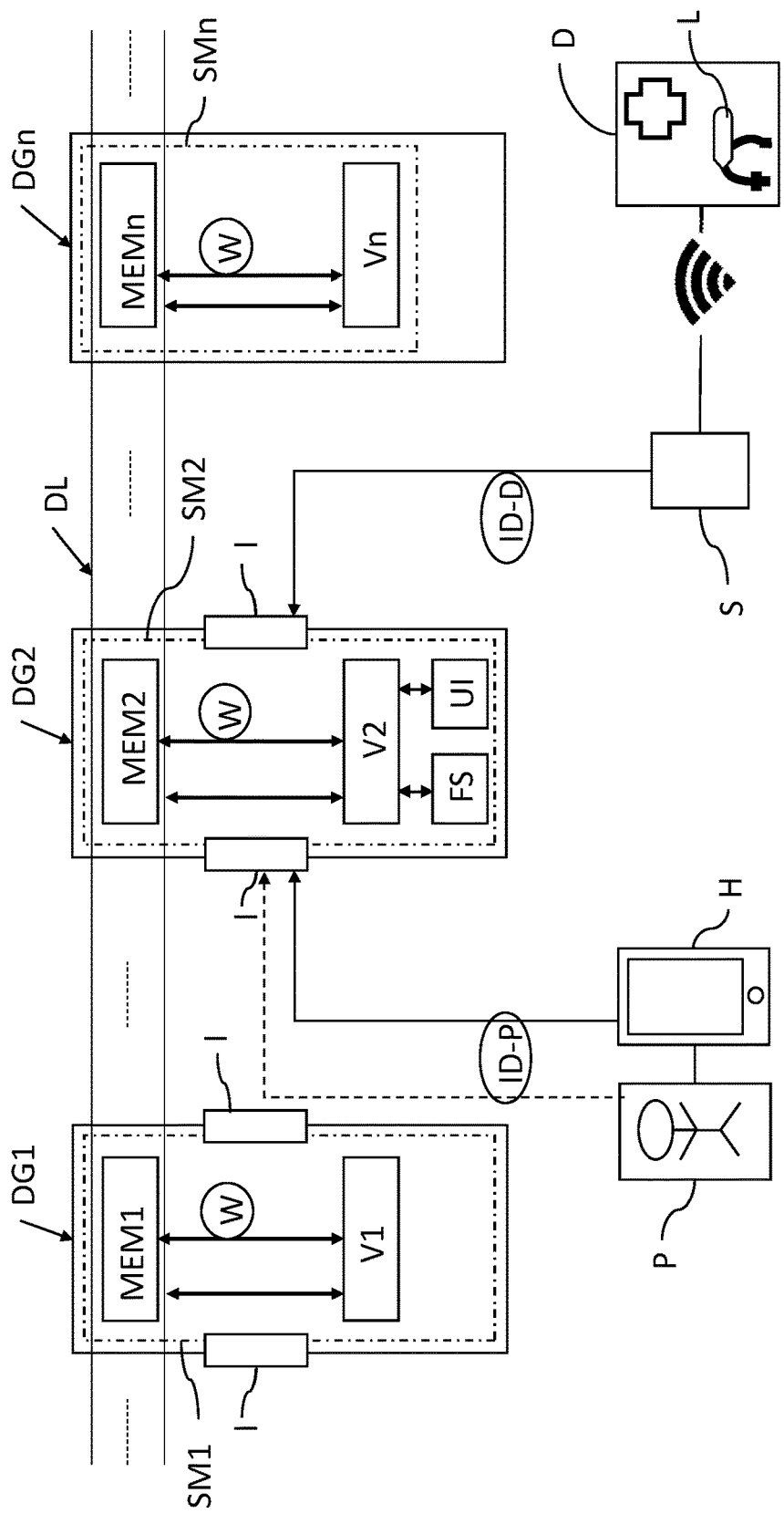
FIG. 1 shows a schematic overview of a distributed memory structure according to a first embodiment comprising a plurality of dialysis apparatuses, at which different patients can be treated.

The disclosure serves to increase the security of the operation of dialysis apparatuses DG which have to be operated with disposables, such as single-use articles (e.g., dialysers), or other medical apparatuses, such as, e.g., reverse osmosis units which are operated with membranes.

In a first embodiment, a first linking partner relates to a patient who can be uniquely identified via a code or identifier of an identification means, such as, e.g., a patient card, and registers at the dialysis apparatus using his identifier. A dialysis kit provided for treating the patient constitutes a second linking partner. The background of this embodiment is that the item of use, e.g., in the form of a dialyser/tube kit, is provided to the patient for use at his own responsibility, and the patient then registers with this kit at any dialysis machine of his choice in order to perform the treatment. Depending upon the application, the item of use is to be used only once or only for a limited number of repetitions, but in any event only for the same patient, e.g., in order to prevent transmission of pathogens between two patients, which under certain circumstances, are also not completely removed by cleaning or disinfection of the disposable which is reusable to a limited extent. This embodiment solves the problem by providing a documentation method which is extended such that repetitions of linking events can be documented and/or verified in a tamper-proof and anonymous manner, and it is possible to verify whether a specific linking partner has already been involved in a linking event. It is also possible to ensure that already linked partners cannot otherwise be linked. For reasons relating to the risk of infection, the item of use must never be swapped from one patient to another. This embodiment provides a system by means of which this can be ensured automatically. This is guaranteed, e.g., by an apparatus in a medical-technical context, in which the disposable is to be used. The apparatus checks independently and automatically the reliability of a linking between the linking partners and can possibly prevent or restrict a treatment.

In a second embodiment, the first linking partner relates to a membrane which is to be operated in a reverse osmosis unit (i.e., a second linking partner). The membrane is marked and can be identified in a unique manner, e.g., by an electronic identification marking via an RFID chip. The identification marking can be read-out by a reading apparatus formed, e.g., on the RO unit and can be provided in the form of a digital identifier for further processing. The membrane is registered at the reverse osmosis unit, so to speak, with this identifier. In the case of this embodiment, it is necessary to monitor that the reverse osmosis unit is always operated in a reliable manner and the disposables (e.g., membrane) are thus not used beyond the designated usage time period. Therefore, the documentation method proposed in this case is extended such that a specific number of identical linking events can be permitted but all further linking events are prevented. If, e.g., the osmotic membrane is used for longer than designated, the water quality can no longer be guaranteed and the dialysis machine which is supplied via the reverse osmosis unit can no longer be operated according to the safety standards. The osmotic membrane which in the reverse osmosis unit allows the passage only of carrier liquid (solvent) and retains the dissolved substances (solute) must be able to withstand these high pressures. If the pressure difference more than compensates for the osmotic gradient, the solvent molecules pass through the membrane in the same manner as with a filter, whereas the "impurity molecules" are retained. The membranes are thus very sensitive. In order to prevent damage to the membrane, filters can be connected upstream. A fine filter can prevent mechanical damage, an activated carbon filter can prevent chemical damage (e.g., by chlorine).

Basically, the solution proposed in this case is geared towards documenting an event which represents a linking of two linking partners (e.g., item of use/disposable and patient who uses the disposable during his dialysis treatment). Specifically, such a linking event can represent, e.g., the case where a person uses an item of use, for instance a dialyser, during a treatment (also referred to as disposables in the context).

In one further embodiment, it is not only possible to document the operation of the apparatus, but also, the apparatus can be safeguarded against an unauthorised use of disposables on the apparatus. If an intended linking event of two linking partners has been evaluated as being not authorised, then the apparatus can be disabled at least for precisely this use with the two linking partners. However, in emergency situations, it is possible to provide a manual special permission by means of manual override. For this purpose, it may be necessary to input a pre-defined enable code on the apparatus.

It is required that the respective linking partners can be identified in a unique manner by an identification marking or an identifier allocated thereto. For instance, the patient can be identified by his patient card, and the dialyser the patient carries around with him can be identified by an RFID chip which is non-detachably connected thereto. Likewise, the membrane can be identified by an RFID chip which is non-detachably provided thereon.

The linking event is documented in that
a) a first mathematical function f is applied to the first identifier (e.g., ID-D): f(ID-D)
b) a second mathematical function g is applied to the second identifier (e.g., ID-P): g(ID-P)
c) f(ID-D) and g(ID-P) are linked mathematically (by applying a further calculation rule φ (RV3, abbreviated to φ)): f(ID-D)φg(ID-P) in order to calculate a documentation value W. By applying the functions, the identifiers of the linking partners are introduced into the documentation.
d) In a general form, the documentation value is extended by a parameter k:

$W=f(ID\text{-}D)\varphi g(ID\text{-}P)\varphi k$

[when k=1, the case is then produced from c)]

e) The calculated documentation value W is written to a memory MEM.

The first and second mathematical functions can be identical.

In the simplest case, f is a multiplication by 1, then f(ID-D)=ID-D. In one case, f is a cryptological function or a hash function (also erratic value function), such as, e.g., SHA, SHA-1, MD5. Other functions are conceivable.

The same applies analogously to g.

The same also applies analogously for the further calculation rule RV3φ.

In an exemplified embodiment, f, g, φ are hash functions, and the generated documentation value has a fixedly defined length and represents quasi a fingerprint of the identifiers. The resulting documentation value W=f(ID-D)φg(ID-P)φk is valuable in cryptological terms and cannot easily be predicted or attributed to the initial values ID-D and ID-P. This has the advantage that the actual ID (ID-D or ID-P) would not be recognisable in clear text in the data record, which meets increased demands relating to the protection of privacy and also makes it more difficult to falsify the serial numbers of the disposables.

In an exemplified embodiment, the identifiers ID-D and ID-P are generated uniquely and in a manner which is difficult or impossible to predict, e.g. using an access generator.

If a multiplicity of disposables D_1 to D_1000 is now provided, all of these disposables have different unique identifiers ID-D_1 to ID-D_1000 which cannot be guessed or predicted.

Moreover, if a large number of persons P_1 to P_1000 are now allocated different, unique identifiers ID-P_1 to ID-P_1000 which cannot be guessed or predicted, this represents the starting position for the last-mentioned preferred exemplified embodiment.

For each random combination of linking partners (D_i, P_j), this idea results in a unique, cryptologically secure, unpredictable documentation value W=f(ID-D)φg(ID-P)φk. By selecting suitable cryptological functions for f, g and φ, it can be rendered randomly difficult to practically impossible to back-calculate to the original values. The calculated documentation values W thus represent a unique pattern or a unique signature of the linking partners involved in the linking event.

An attacker who does not know an identifier will have to employ a great deal of effort in order to guess a meaningful combination because the identifiers cannot be guessed easily. In contrast, this is easy for an apparatus which can read-in the identifiers of two linking partners locally. This has the technical advantage that a read access to a distributed memory structure DL can be performed very efficiently.

Storage of the calculated documentation values W/patterns:

These documentation values W (also abbreviated hereinafter to: values) must be stored in each case after being calculated. In the simplest case, this can simply be the value itself. In extended variants, time stamps or further data can also be stored with the pattern.

All of the values W of a specific method are stored in a common data structure which is arranged as a distributed ledger DL.

In a variant, the properties of the identifiers (ID-D, ID-P) and the functions f, g, φ are selected such that all of the values which can be generated by the method have a constant size and/or a constant format. This gives rise to storage with blocks of equal size. Optionally, padding with zeros or ones to the uniform block size may be necessary.

In a variant, there are memory blocks which store a single value W in each case.

The storage can take place locally in a terminal which performs the method (e.g., dialysis apparatus, reverse osmosis unit, mobile terminal of a user). The storage can take place remotely in the Cloud, on a server, or in a back end, wherein in the last case a local gateway apparatus is required. Preferably, the storage takes place such that all of the apparatuses involved store the patterns locally directly after generation and then distribute them to apparatuses connected in the network. This procedure is defined as "synchronised storage".

For example, there is a multiplicity of apparatuses which are connected in a network, perform the method, and incrementally synchronise their memories, e.g., via the Internet with the aid of, e.g., a peer-to-peer communication such that after a certain amount of time all of the generated values i are present in the local distributed ledger DL of all of the apparatuses. A network which is constructed in such a manner does not require any central entities.

Alternatively, the distribution of the patterns to the apparatuses connected in the network can be controlled by means of an algorithm such that not every apparatus stores all of the patterns but all of the patterns are stored at least once, e.g., redundantly, within a defined group of communicatively connected apparatuses. The distribution of the patterns for storage can be performed according to fundamentally known methods without a dedicated central administration master. Preferably, a storage procedure can be performed repeatedly, in connection with identifiers used with an apparatus, in a local manner in this apparatus in order to reduce the network traffic.

Preferably, a distributed ledger technology is used in order to reach agreement on all of the linking events within the apparatus network which are documented by the values W and to update these values W in the network. This produces a decentralised linking event database.

Preferably, there is a consensus mechanism for guaranteeing identical copies of the distributed ledger DL on all entities involved.

Processing the Stored Patterns:

If there is a desire to create a linking event (such as, e.g., a dialysis treatment) and the identifiers of both linking partners are known (ID-D, ID-P), the method can be carried out with one apparatus and the pattern or the calculated documentation value W relating to these partners is obtained. Then, the distributed ledger DL can be searched to find out whether precisely this value W is stored therein. In so doing, it is crucial that the value can be stored not locally but instead on another entity of the distributed ledger DL, e.g., on another apparatus, and this is also detected automatically by querying the distributed ledger DL.

If the sought value W is not found, this means that a linking event of these two linking partners is not yet documented. In a simple embodiment, the value is thus deemed to be validated.

If the sought value W is found, this means, in an embodiment, that there has already been a linking event of these two linking partners. In one variant, this can result in no further linking event being permitted and the value not being validated. The operation of the apparatus can be disabled automatically in response to the authorisation not being provided.

The requirements to be met by the apparatuses performing the method are as follows:

they must be able to gain knowledge of ID-D (by means of manual input, scanner for bar code or QR code, RFID reader, image recognition, data reception)

they must be able to gain knowledge of ID-P (by means of a patient card reader and the above-described methods) they must have a communication connection.

They must have a memory.

The cryptographic calculations can be performed locally or remotely. If they are to be performed locally, the apparatus must naturally be capable of calculating, i.e., must know the calculation rule and have sufficient processor and memory resources.

The Internet connection can be established directly or via intermediate entities (such as e.g. local WiFi).

The apparatuses can be, e.g., a treatment machine (e.g., dialysis apparatus DG), a smartphone, and/or a tablet as a gateway which enables a treatment.

Documenting of Repetitions of Linking Events:

With the basic method, the values W of two linking events of the same linking partners look identical because for both events the calculation would be $f(ID-D)\varphi g(ID-P)\varphi k=W$.

Therefore, the method is extended in order to make such repetitions distinguishable. If the repetitions are distinguishable, they can be documented and the number of repetitions can be ascertained.

This problem could be solved by means of blockchain methods, in that a value $W(n+1)$ is computed by hashing the value $W(n)$. This would then be $$W(1)=f(ID-D)\varphi g(ID-P)$$

$$W(2)=W(1)\varphi f(ID-D)\varphi g(ID-P)$$

$$W(3)=W(2)\varphi f(ID-D)\varphi g(ID-P)=W(1)\varphi f(ID-D)\varphi g(ID-P)\varphi f(ID-D)\varphi g(ID-P)$$

$$W(n+1)=W(n)\varphi f(ID-D)\varphi g(ID-P)=n+1 \text{ times performed } f(ID-D)\varphi g(ID-P).$$

Although the method could be cryptologically feasible and distinguishable, it would be extremely complex in particular to verify in advance which input values are suitable for this purpose and which result in ambiguous results ("collisions") or interruptions. Moreover, it does not provide any shortcut for calculating how many repetitions have already taken place. The hash function would have to be repeated by brute force for as long as until a comparable result is no longer found in the distributed ledger.

Therefore, the present disclosure proposes another concept. To this end, the parameter k which is introduced is a third identifier ID-n which denotes the repetition. In the simplest case, ID-n is simply the natural number n which corresponds to the repetition of a linking event.

However, it is also feasible to have, e.g., a table which allocates an identifier ID-n to each n. In this case, it is important that all of the entities involved in the method allocate an identifier ID-n to a repetition value n in the same manner. In other words: it must be predictable to ensure that all of the apparatuses and entities involved can "swing" without external interference from the value of one repetition to the next.

The thus computed values $W=f(ID-D)\varphi g(ID-P)\varphi k$ are then either a) where $k=ID-(n+1)$:

$$W(n+1)=f(ID-D)\varphi g(ID-P)\varphi ID-(n+1)$$

b) where $k=h(ID-(n+1))$:

$W(n+1)=f(ID-D)\varphi g(ID-P)\varphi h(ID-(n+1))$, wherein h could be a cryptological function similar to f and g.

c) Or, if an increased security chain of the documentation of chain is still desired (as with blockchain) $W(n+1) = W(n) \varphi f(ID\text{-}D) \varphi g(ID\text{-}P) \varphi h\ (ID\text{-}(n+1))$.

When selecting suitable values for ID-n, it is thus possible to ensure that the values W relating to different repetitions (i.e., with different repetition numbers n) are different.

In the variants a) and b), the entire series of values relating to different repetitions would not even have to be calculated in order to calculate a new value W relating to the current repetition.

If an apparatus does not know how many repetitions have been performed and wishes to ascertain this, it can consecutively compute different values W relating to the present linking partners and search through the distributed ledger DL for the values W. The value W relating to the highest repetition number n found during the search corresponds to the number of previously performed and documented repetitions.

Verify Whether a Linking Partner is Already Linked:

A practical case for applying one development of this method is to ensure that a specific disposable D (e.g., a dialyser) which is suitable and designated for repeated use is used only by the same person P. The method shown above can be used to generate a linking result of two linking partners and to document and ascertain the repetition of an identical event.

However, if a disposable D is linked initially to a first patient P_1, there is no indication in the above methods that it should not be linked (in an authorised manner) to a second patient P_2.

In the case of one variant for ensuring that one partner D linked once to a first patient P_1 cannot be linked to a further partner P_2, but instead can be (repeatedly) linked only to the partner P_1, the method is extended as follows:

For the very first linking of a disposable D, two values W(n=0) and W(n=1) are generated and stored in a common data structure in the distributed ledger DL. W(n=0) is generated only in dependence upon ID-n and ID-D:

$$W(n=0)=f(ID\text{-}D) \varphi h(ID\text{-}n(n=0))$$

However, in order to generate W(n=1), ID-P is used again:

$$W(n=1)=f(ID\text{-}D) \varphi g(ID\text{-}P) \varphi h(ID\text{-}n(n=1))$$

The following values W (n>1) are generated as usual.

If any entity in the network now scans an ID-D and applies the method, firstly the value W(0) is generated and searched for in the distributed ledger DL. If the value is found, it is clear that the single permissible combination of ID-D and ID-P is stored in the form of W(1) directly behind it. If a linking partner P wishes to create a linking event with precisely the same disposable having ID-D, the apparatus scans its ID-P and calculates the value W(1) relating to this combination of linking partners. If this value W(1) matches the value which is stored behind the found value W(0) relating to the disposable having the identifier ID-D, it is thus clear that it is the same linking partner P as in the documented linking event W(1).

If the calculated value W(1) does not match the stored value W(1), the involved linking partners P are not identical.

In the above example, the apparatus would thus output an error message and disable the apparatus or refuse the start-up thereof. In addition, still further measures can be triggered, such as requiring, e.g., a manual overwrite or a manual override for start-up (which, in turn, would be documented in a tamper-proof manner), sending an error message to a backbone, calling the nurse, and/or the like.

In one development, the linking logic is reversed and only those linkings which have not taken place are allowed.

Maximum Repetition Number and Interruption:

A further development of the method renders it possible to allow a specific number of repetitions n_max and thereafter (n>n_max) to no longer permit any further repetitions of the linking events.

In a simple variant for accomplishing this, the involved entities would know a maximum number—either locally or in the apparatus network or in the case of a central entity, n_max would be stored. This scenario could carry a risk of attack especially in the case of local storage. However, in each case repetitions above the maximum are also documented in the distributed ledger DL and liability could be excluded.

In one development, the number n_max is a specific property of the linking partner D and is contained cryptologically in its identifier ID-D, e.g., as a checksum.

In one development, the number of repetitions n_max is fixed specifically for each linking partner P and is coded in its identifier ID-P.

In one development, the number of repetitions is dependent both upon P and upon D and from a space of possible maxima a value is determined in dependence upon ID-D and ID-P.

In one development, the identifiers ID-n of the repetition number n is defined only for a specific amount n up to a selected n_max, e.g., for n element from (1-10) to n_max=10 or for n element from (0-3) with n_max=3. If an entity now attempts to generate a value W(n>n_max), it will fail because it cannot generate an identifier ID-n for n>n_max. An error will occur which can be output and/or documented as "number of maximum repetitions reached" on a user interface, optionally followed by an interruption or a warning that the guarantee expires, etc.

In one development, ID-n is formed with a function to n which does not provide a result or meaningful result for values of n>n_max. For example, ID-n could have a function t(n) which provides real results for n=0 to n=n_max=10 and provides imaginary results for natural numbers n greater than 10:

$$t(n)=\sqrt{(9.99-n)}$$

Alternatively, in the variant relating to the above-described verification as to whether a linking partner is already linked, a linking with ID-n (n=n_max) could be performed immediately after generation of the value W(0) and could be counted down for each further use. Then, when n=1 is achieved the maximum permissible number of re-uses would be achieved and during the next decrement (n=0) the function could throw out an invalid result.

Further Examples of Use

The first application is the multiple use, e.g., of a dialyser which currently is typically designated only for one-time use. For various reasons relating to hygiene and health, it is desirable that a dialyser is used multiple times—if at all—only by the same patient. Therefore, it is desirable to document links of patient ID and dialyser ID/disposable (one-time product) ID. It is not relevant that the same dialysis machine is used for this purpose. However, it would be feasible and could also be documented in developments. Further parameters which could be documented are treatment duration and further treatment parameters, as well as a permissible use time after the first use. However, this is not within the core concept of this method. However, the method can ensure that only the number of repeated uses of the same dialyser, as determined by a doctor, is possible, e.g., five repetitions.

A further application for this method is therapeutic apheresis. This is an apparatus-based treatment to remove pathogenic substances from the blood with the aid of filters and adsorbers. The further application described hereinafter relates to the use of an adsorber during the operation of a plasma filtration apparatus and an immune apheresis apparatus and the secure documentation thereof.

An adsorber can be reused as a disposable for the same patient—even multiple times during a single treatment. Each patient can use at least one adsorber which can be refreshed. For example, two adsorbers can be operated alternately as an item of use. The first adsorber is used and the second is regenerated (with sodium chloride) at the same time. Since the adsorber is a cost-intensive product, the motivation to use the disposable multiple times is high and in particular for:

multiple use during the individual treatment session and
multiple use in several treatment sessions.

During use of the adsorber, it is essential to check how long it has been used or how it can still be used in an authorised manner.

Basically, the method and system presented herein render it possible to verify an operating time of the disposable (whether this is a membrane, dialyser or other type of medical disposable). Linking events can be detected in a timed manner (e.g., one linking event per hour or per minute) in order to be able to document and/or supervise the re-use of disposables in the apparatuses. The background to this is that such a membrane is not inserted for each treatment but instead is done so for a specific time period which is generally longer than a treatment cycle. Therefore, a new linking event is detected or validated per pre-defined unit of time, e.g., one linking event per hour. The detection of linking events comprises the method step of validating.

A further application is a dialyser-like filter which is used in treatment apparatuses in addition for filtering dialysis water or dialysis liquid. Such filters filter out and retain bacteria, viruses and endotoxins from the liquids. These filters may only be used to a limited extent. The limitation can relate to the number of permissible repetitions, a time period, a limitation in terms of the use for a patient, or other aspects. This application is an example of the fact that several (in this case: three) different (use) criteria are to be applied cumulatively in order to authorise the operation of the apparatus with the disposable (in this case: filter). The three different criteria for maximum use are maximum number. For example, such a filter is allowed to undergo a maximum of a fixed number of chemical disinfection cycles, e.g., by means of chlorine or hypochloride.
Maximum operating time. The filter is allowed to have been in use only for a fixed maximum operating time.
Maximum service life. The filter is allowed to reach a specific maximum service life, i.e., an upper time limit is reached if the filter has been installed in an apparatus for a specific time period—irrespective of whether it was in operation or has been chemically disinfected.

In an embodiment, provision is made that in a preparatory configuration phase of the method, criteria can be configured which can be specified by the operator or can be selected form a pre-defined menu and which are monitored for compliance automatically during the operation of the apparatus.

In other applications, only two or other criteria for the permissible use of the disposable can also be defined and checked. This exemplified embodiment is intended to illustrate that the method can also be used for documenting and/or supervising a plurality of types of linking events. For this purpose, the apparatus requires a plurality of different identifiers—depending upon the role: a first identifier for linking events relating to the operating time of the linking partner, a second identifier for linking events relating to the disinfection procedures of the linking partner, and a third identifier for linking events relating to the service life of the linking partner. Therefore, it is possible to document all three use criteria or types of procedure. The method which is to prevent a use above the permissible upper limit of repetitions ensures that for all three parameters a verification is performed as to whether the maximum number of repetitions is reached.

Furthermore, for each disinfection procedure the apparatus creates a linking event with a machine disinfection identifier and the filter.

In addition, the apparatus creates a linking event with a machine operation identifier and the filter for each unit of time commenced during operation.

For instance, for the pairing consisting of machine identifier service life and filter identifier a linking is thus detected during insertion of the filter into the apparatus and, if the filter remains therein, is detected in a fixed time interval, e.g., one linking per week. Alternatively, only when a filter is inserted for the very first time is a linking event with the service life identifier of the apparatus detected—and a time stamp in the distributed ledger is used to ascertain whether the filter is still allowed to be used or not. In the case of the product DiaSafe, the maximum allowed service life is, e.g., about 12 weeks—otherwise the risk posed by germ infestation and microbiological growth is too great. The latter case would ensure that, in the event of a failure of a machine which is then thus no longer able to document any further service life links, the service life is still not exceeded.

Although the filter can be used in different apparatuses, all of the relevant linking events can be monitored and documented because all types of events are linked to the unique filter identifier and so any exceeding of the permissible operating parameters can be documented, verified and possibly prevented.

In the case of this application, a plurality of chains are linked such that there are a plurality of partial chains for one filter identifier, one for each identifier type (operating time, disinfections, service life) as it were. Such an interrelated verification is only possible if the apparatuses performing the method in accordance with the invention have knowledge about which chains belong together, i.e., in this case, which three chains belong to the same disposable. In this sense, the chains must be linked together at least to such an extent that the apparatus can detect the relevant data. The linking can be accomplished, e.g., via a set of functions f1, f2, f3, by means of which three different headers are generated from one disposable ID (ID-D)—one for each of service life f1(ID-D), operating time f2(ID-D) and number of disinfections f3(ID-D). If the relationship between f1, f2 and f3 is comprehensible and systematic, the chains can also be detected in this manner as being linked if the relationship between f1, f2 and f3 is known. In realistic applications, the functions should have such a systematic relationship.

A further application for this method is the documentation of the use of a membrane for water purification by means of reverse osmosis (RO). Specifically portable apparatuses could possibly use membranes which can be used only for, e.g., 500 or 5000 operating hours. In this case, smaller units could be documented, i.e., a repetition would then not be a use but instead an entry is created relating to an increasing n per operating hour commenced or per operating minute commenced, for flow volumes, etc.

For the sake of completeness, it may be stated that a simple but feasible case is W=f(ID-D)φg(ID-P)φk where f, g, φ=1, i.e.

$$W = ID\text{-}D * ID\text{-}P * k$$

The invention will be explained even more precisely hereinafter with reference to exemplified embodiments in conjunction with the figures.

FIG. 1 thus shows an example of a method for safeguarding dialysis apparatuses DG against an unauthorised use. An unauthorised use is when the same disposable is to be used, e.g., for different patients or if a disposable is to be used over and above the number of maximum permissible uses. A group of dialysis apparatuses DG1, DG2, . . . DGn is connected in a cluster of apparatuses via a peer-to-peer network. The dialysis apparatuses DG can be arranged, e.g., in a dialysis center. They can also be located in different institutions distributed worldwide. As participants in the safeguarding methods, each dialysis apparatus DG comprises a safeguarding module SM. The safeguarding module SM can be implemented directly on the dialysis apparatus DG or on a gateway which is allocated thereto and exchanges data therewith. The safeguarding module SM can interact with an enabling/disabling signal transmitter in order to enable or disable the dialysis apparatus DG for the intended treatment with the patient P and the disposable D. Moreover, the safeguarding module SM can be designed having a user interface for displaying the result or partial result (e.g., of the calculated documentation value). The safeguarding module SM can comprise the following components:

1. A read-in interface I. There can also be two entities of the read-in interface, as schematically illustrated in FIG. 1: a first entity of the read-in interface I which is intended to read-in the patient identifier ID-P, and a second entity of the read-in interface I which is intended to read-in the disposable identifier ID-D.
2. A digital processing unit V which can be designed as a processor, a chip, or circuit arrangement and serves to perform the securing method on the basis of the read-in identifiers ID-P, ID-D (or ID-M, ID-RO) and which exchanges data with a local memory MEM of the apparatus DG and with the distributed memory structure DL, and possibly with further modules.
3. The memory MEM;
4. Optionally, in addition to the medical operating modules, still further processors and further modules can be provided on the dialysis apparatus. Therefore, the containment line of the aforementioned modules is illustrated in FIG. 1 as a dot-dash line.

All of the memories MEM1, MEM2, MEMn of the respective dialysis apparatuses DG1, DG2, . . . DGm form the distributed memory structure which can be designed as a distributed ledger.

The patient P must initially register and identify himself at the safeguarding module SM or at the dialysis apparatus DG and provide the dialysis apparatus DG with his (first) identifier ID-P. Basically, different options are available to him for this purpose. He can thus activate or call up, e.g., an app on his mobile apparatus H (e.g., smartphone, tablet) which invites him to input his patient identifier ID-P. Otherwise, the apparatus H and/or the dialysis apparatus DG can be designed having a reading means or a device (e.g., code scanner) in order to read-out the patient identifier ID-P as a code, e.g., from a patient or health card. The code (e.g., bar code) located on the card then corresponds to a physical "identification marking" of the patient P which, for the purpose of further processing, is then transformed into the digital identifier ID-P identifying the patient and corresponds thereto. Furthermore, he can also input his first identifier ID-P as it were manually on the apparatus DG directly via a user interface UI. This is illustrated in FIG. 1 by the broken line.

In a corresponding manner, the second identifier ID-D of the disposable D is detected. For this purpose, the disposable D can be designed having an RFID identification marking or differently designed label—marked with the letter L in FIG. 1—which is detected by a reading apparatus, in this case a scanner S, and is fed in the form of the digital second identifier ID-D via the read-in interface I to the processing unit V for further processing.

After the first and second identifiers ID-P, ID-D have been read-in via the read-in interface I, they are provided to the processing unit V which applies a first calculation rule RV1 to the first identifier ID-P and a second calculation rule RV2 to the second identifier ID-D in order to process the resulting two partial results with a third calculation rule (designated as RV3 in FIG. 3 and in the text also as φ) in order to calculate the documentation value W.

As can be seen in FIG. 1, the dialysis apparatus DG and in particular the safeguarding module SM (illustrated by way of example in FIG. 1) can also comprise a user interface UI and an enabling and/or disabling unit FS which enables the apparatus DG only in the event of authorised linking for the operation with the respective linking partners D, P. If no authorisation can take place, the operation of the apparatus can be disabled at least for the two respective linking partners D, P. For this purpose, a corresponding indication can be output on the user interface UI which denotes the reason for the disabling (e.g., "item of use has already been used for another patient" or "permissible maximum number of use repetitions for the item of use is reached").

If the method is to be used as a pure documentation method, the documentation value W thus calculated can now be written directly to the memory MEM.

If the method is to be applied as a safeguarding and authorising method, the calculated documentation value W cannot be written directly to the memory MEM, but instead firstly a validation is performed. The validation can be performed by means of a consensus algorithm which includes an access to the distributed memory structure DL in order to check whether the documentation value W relating to the item of use is already stored in the memory structure DL and, if so, with which repetition value. Depending upon which rules have been configured in a configuration phase in advance, in particular if said documentation value is not yet stored (new linking event) or if it has been stored for the same patient but within the maximum permissible repetition rate (permissible re-use), the respective documentation value W is deemed to be validated; otherwise it is not. Only when validation is successful is the documentation value W stored in a synchronised manner in the distributed ledger structure DL and the operation of the apparatus can be authorised for the respective linking partners D, P.

Figure 2:
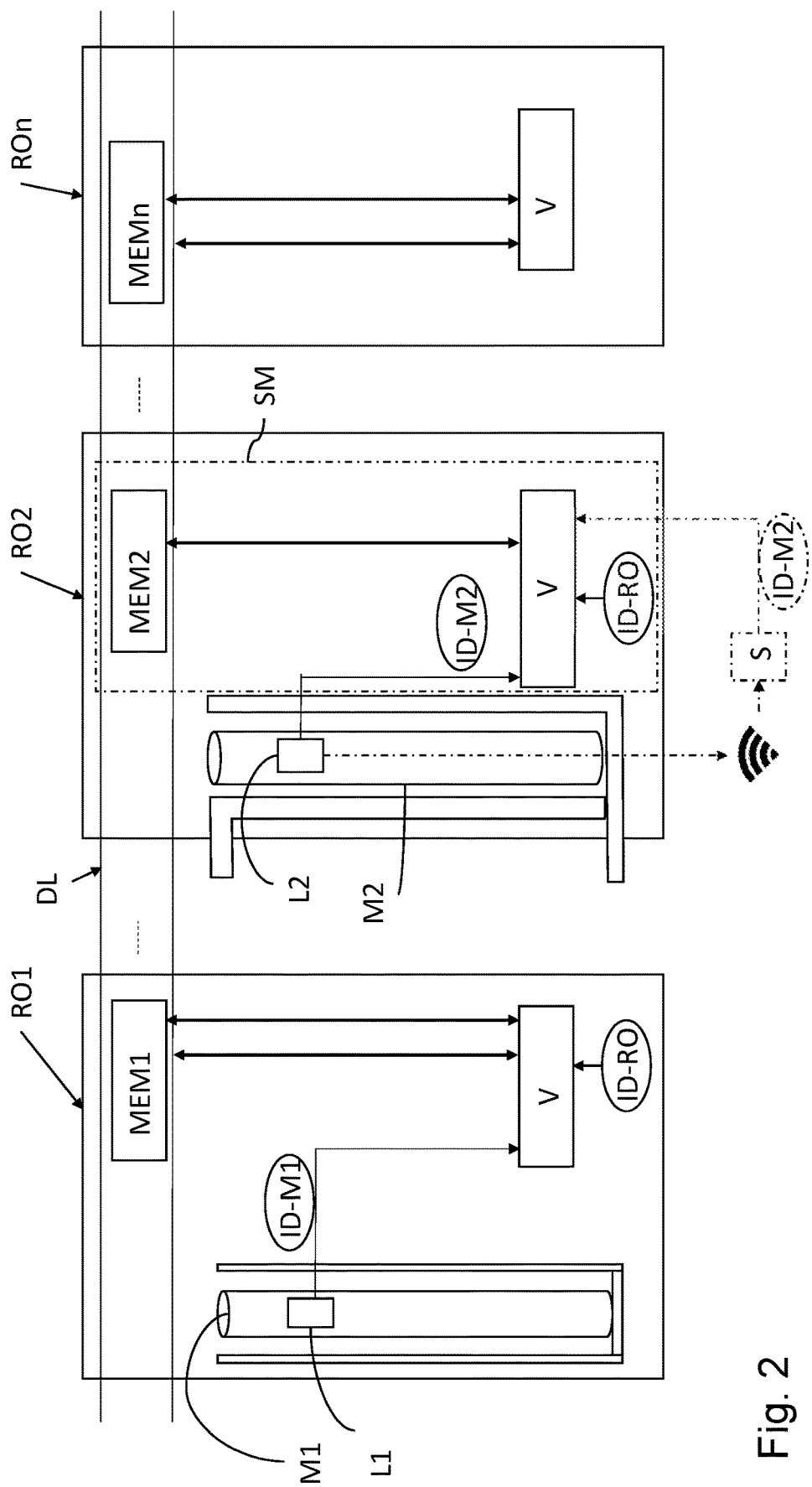
FIG. 2 shows a schematic overview of a distributed memory structure according to a second embodiment comprising a plurality of reverse osmosis units which can be operated with different membranes.

FIG. 2 shows a further exemplified embodiment. In this case, the intention is to monitor whether a reverse osmosis unit RO is operated in a permissible manner. The reverse osmosis unit RO serves to provide treated, purified water for use for a dialysis apparatus DG. It is based upon the principle of reverse osmosis and for this purpose comprises pumps and filters, receptacles for the liquids and a membrane M as an item of use. The components of the unit RO are illustrated only schematically in FIG. 2. The safeguarding method serves to verify whether the disposables used therein and used in the apparatus RO, such as the membrane M, are still allowed to be used and as yet have not been used too often. To this end, the reverse osmosis unit RO is designed having a processing unit V and the item of use, e.g., the membrane M, is marked with a physical label L (bar code, RFID code, etc.). The first identifier ID-M, ID-M1, ID-M2 etc. is allocated in a unique manner to the label L or n can be transformed into this. Alternatively and as illustrated in FIG. 2 by a dot-dash line, the label L can be read-out by a scanner S and can be fed in the form of the first identifier ID-M2 to the processing unit V for further processing. The first identifier ID-M is a digital data record and is processed by the processing unit V by means of algorithms provided. Furthermore, the second identifier ID-RO of the RO unit is fed to the processing unit V in order to apply the calculation rules RV1, RV2, RV3 to the data records.

The label L of the membrane M is detected (e.g., via a scanner S) and is read-in as the first identifier ID-M and the ID code ID-RO of the reverse osmosis unit RO is read-in as the second identifier. Now, substantially the same method as described above in conjunction with FIG. 1 is performed in order to authorise or disable the operation of the apparatus of the reverse osmosis unit RO having the membrane M.

Figure 4:
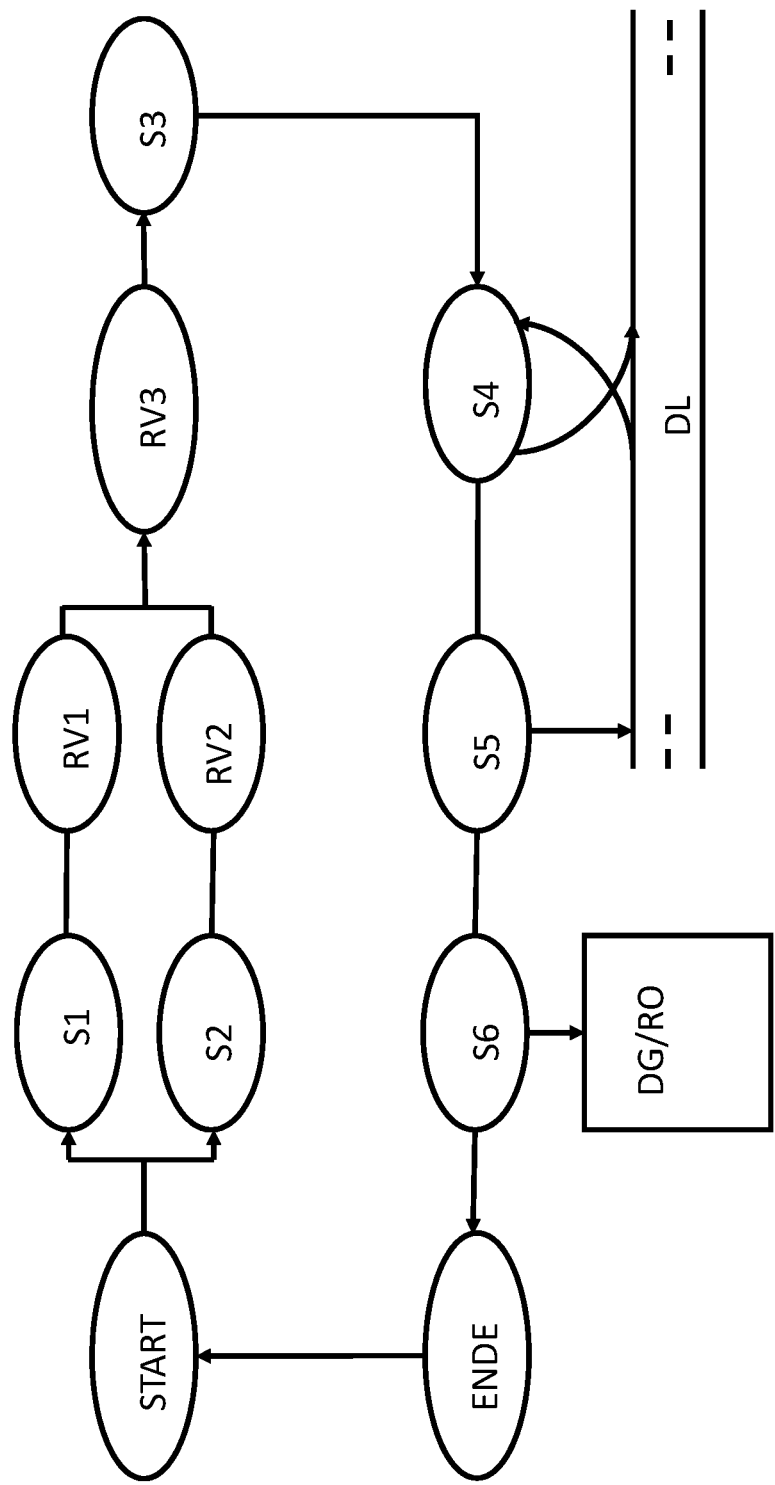
FIG. 4 shows a flow diagram of a method according to an embodiment.

In the above-mentioned examples, it is obvious to the person skilled in the art that the first identifier and second identifier can also be exchanged. As also indicated in FIG. 4, the two identifiers ID-P, ID-D, ID-RO, ID-M can also be detected in parallel or in another time sequence.

As indicated in FIGS. 1 and 2 by way of example for the first apparatuses DG, RO, the calculated documentation value W is initially intermediately stored in a local buffer memory. Then, a validation can optionally be performed, authorising the operation of the apparatus with the respective linking partners D, M. This can be performed by an access to the distributed data structure of the distributed ledger DL. This means that impermissible linking attempts are not even stored at all in the distributed data structure DL and instead only those which could be validated successfully are stored therein.

Figure 3:
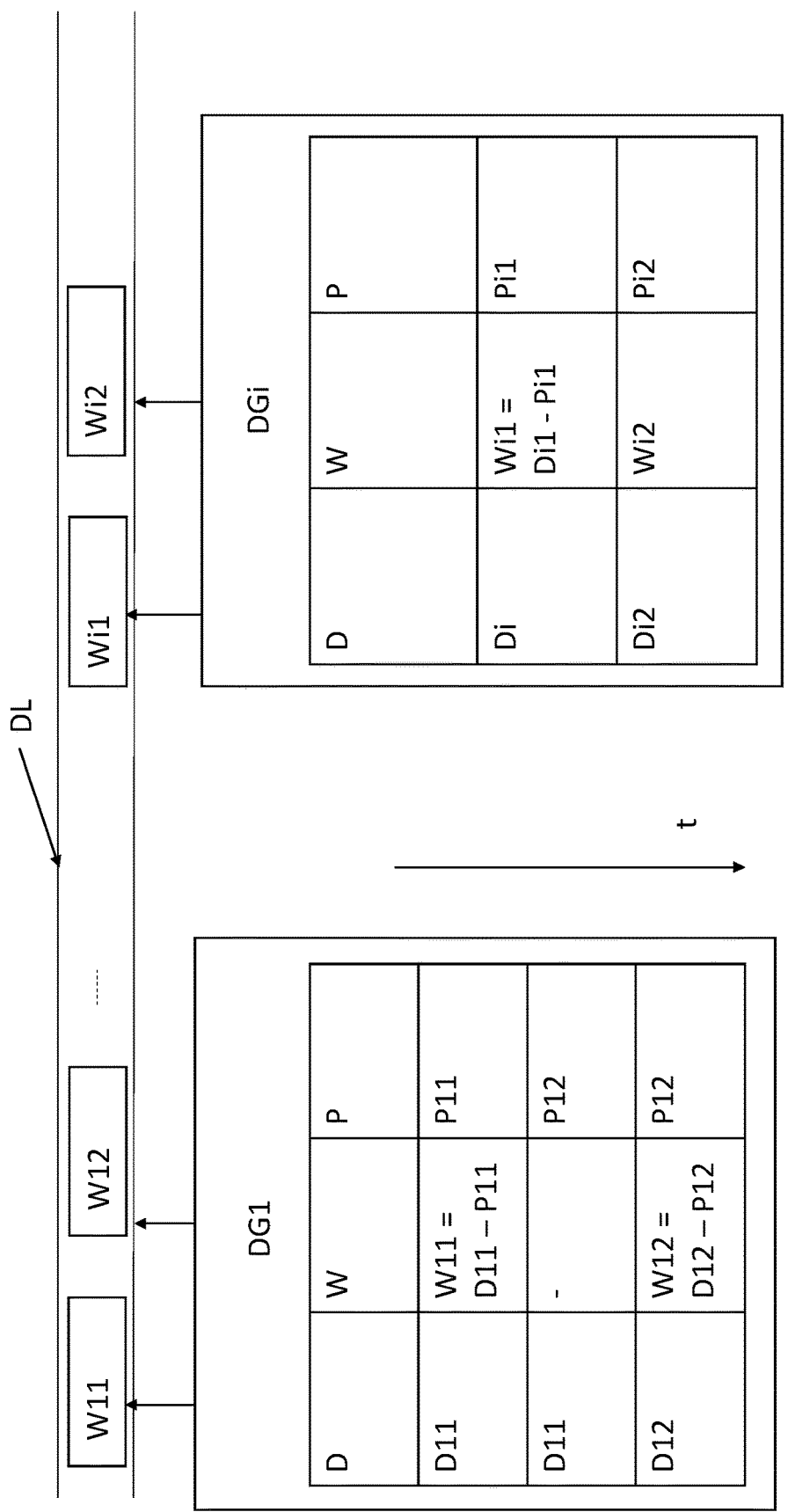
FIG. 3 shows a schematic view for interaction and the exchange of messages between the apparatuses and the distributed memory structure.

FIG. 3 shows a schematic view of the exchange of data and the allocations of the data records. On a first apparatus DG1, different patients P are treated one after the other using different disposable kits D. The time is plotted in FIG. 3 from top to bottom according to the arrow direction. A first patient P11 thus uses a disposable D11 on the first apparatus DG1. The documentation value W11 is calculated as described above and is validated by the consensus algorithm. Since it is not yet stored, it is entered into the DL structure DL. Then, another patient P12 wishes to use the same disposable D11 (in this example on the same dialysis apparatus DG1). The calculated documentation value W is not stored because it could not be validated because the same disposable has already been used for another patient (P11). A further patient P13 now wishes to use a disposable D12. This is evaluated as being permissible and the value 12 is stored in the distributed ledger DL and so on.

All of the apparatuses DG exchange data and access the distributed ledger structure DL. An i-th dialysis apparatus DGi is used by a patient Pi1 with a disposable Di1. This has been calculated as being permissible and so the value Wi1 is stored in the distributed ledger DL. A second patient Pi2 wishes to use the disposable Di2 and accordingly the distributed ledger DL is searched to find the calculated value Wi2.

For the case i=1, the validation in the above example would fail because the disposable D11 has already been used on the first apparatus DG1 by the first patient P11. This is detected directly on the apparatus DGi which can be located, e.g., in Germany, even though the first apparatus DG1 is located, e.g., in Japan.

For the case i=2, the authorisation would be successful because the respective linking events are not yet stored in the distributed ledger DL and therefore a new linking is provided.

In contrast to the validation, the authorisation can include still further verifications (e.g., to verify, by access to a rule base, still further criteria which are stored in the form of rules, such as the type of intended treatment for the respective linking partners, etc.).

FIG. 4 shows the typical sequence of the method of an exemplified embodiment in a flow diagram. After the start of the method, in step S1, the first identifier ID-P is read-in. In step 2, the second identifier ID-D is read-in. Step S1 and S2 can also be performed in a reversed sequence. The first calculation rule RV1 is applied to the first identifier ID-P and the second calculation rule RV2 is applied to the second identifier ID-D in order to provide partial results which are processed by means of a third calculation rule RV3 in order to provide or calculate the documentation value W in step S3. In step S4, the validation of the calculated documentation value W can be performed by executing the consensus algorithm by access to the distributed ledger DL. If the validation is successful, in step S5, the value W is stored in a synchronised manner in the distributed ledger DL, and in step S6, the apparatus DG can be enabled with the respective disposable D as linking partners. This is effected by targeted activation of the apparatus DG, RO. Then, the method can be performed iteratively or can be terminated. The sequence depicted above can be applied both for safeguarding a dialysis apparatus DG with a use of disposables D and for safeguarding a reverse osmosis unit RO with a use of membranes M.

Finally, it is noted that the description of the invention and the exemplified embodiments are fundamentally to be understood to be non-limiting with respect to a specific physical implementation of the invention. All features explained and illustrated in conjunction with individual embodiments of the invention can be provided in different combinations in the subject matter in accordance with the invention in order to achieve the advantageous effects thereof at the same time.

For a person skilled in the art, it is obvious that the invention can be used not just for dialysis apparatuses DG and reverse osmosis units RO but also for other medical-technical apparatuses which use disposables, the use of which is to be verified at or with the respective apparatus. Furthermore, the components of the safeguarding module SM can also be distributed over a plurality of physical products.

The scope of protection of the present invention is set by the following claims and is not limited by the features explained in the description or shown in the figures.

The invention claimed is:

1. A method for safeguarding an apparatus in a medical environment against an unauthorised operation of the apparatus, wherein the apparatus is connected to other apparatuses via a network, and wherein authorisation is dependent upon a linking event between at least two linking partners within the framework of an operation of the apparatus, wherein one of the linking partners is an item of use which is used during the operation of the apparatus, the method comprising:
- reading-in a first identifier for identifying a first linking partner of the at least two linking partners in a unique manner and a second identifier for identifying a second linking partner of the at least two linking partners in a unique manner;
- applying at least a first calculation rule to the read-in first identifier and applying a second calculation rule to the second identifier for calculating a documentation value that defines a unique signature of each instance of a linking event between the first and second linking partners, wherein calculating the documentation value includes calculating a third identifier as a repetition value which uniquely represents a number of repetitions for a linking event between the first and second linking partners so repetitions of linking events can be documented in a distinguishable manner using a unique signature of the linking partners involved in the linking events;
- causing synchronised storage of the calculated documentation value in memories of apparatuses of the network; and
- safeguarding the operation of the apparatus for the first and second linking partners.

2. The method of claim 1, wherein the synchronised storage is effected using a distributed memory structure.

3. The method of claim 2, wherein the distributed memory structure is a distributed ledger structure.

4. The method of claim 3, wherein the distributed ledger structure is implemented in that a data block comprises at least the calculated documentation value and does not contain any reference to other blocks.

5. The method of claim 1, further comprising validating and/or authorising the calculated documentation value by applying a consensus algorithm such that causing and safeguarding are performed only if validation is successful.

6. The method of claim 5, wherein the applying the consensus algorithm comprises:
- accessing a memory of a distributed memory structure of an apparatus in order to check for a specified documentation value whether it is already stored, and only when the result of this check is negative and/or the number of permissible repetition values is less than a pre-definable number thereof, validating the documentation value.

7. The method of claim 5, wherein the apparatus is disabled for the intended operation with the two respective linking partners when the validation is not successful and/or authorisation is not provided.

8. The method of claim 5, wherein the validating and/or authorising the linking event is performed in a timed manner and/or event-based manner.

9. The method of claim 1, wherein the calculation of the documentation value includes applying a third calculation rule to a first partial result, obtained by applying the first calculation rule to the first identifier, and a second partial result, obtained by applying the second calculation rule to the second identifier, for providing a third partial result and a further linking function being applied to the third partial result.

10. The method of claim 1, wherein all of the apparatuses apply the same calculation rules for calculating the documentation value.

11. One or more non-transitory computer readable storage media storing instructions that, when executed by at least one programmable processor, cause the at least one programmable processor to perform operations comprising:
- reading-in a first identifier for identifying a first linking partner of the at least two linking partners in a unique manner and a second identifier for identifying a second linking partner of the at least two linking partners in a unique manner;
- applying at least a first calculation rule to the read-in first identifier and applying a second calculation rule to the second identifier for calculating a documentation value that defines a unique signature of each instance of a linking event between the first and second linking partners, wherein calculating the documentation value includes calculating a third identifier as a repetition value which uniquely represents a number of repetitions for a linking event between the first and second linking partners so repetitions of linking events can be documented in a distinguishable manner using a unique signature of the linking partners involved in the linking events;
- causing synchronised storage of the calculated documentation value in memories of apparatuses of the network; and
- safeguarding the operation of the apparatus for the first and second linking partners.

12. A safeguarding module for an apparatus for the medical environment, the safeguarding module comprising:
- a read-in interface for reading-in a first identifier and a second identifier;
- at least one processor programmed with instructions to perform operations comprising:
  - reading-in a first identifier for identifying a first linking partner of the at least two linking partners in a unique manner and a second identifier for identifying a second linking partner of the at least two linking partners in a unique manner;
  - applying at least a first calculation rule to the read-in first identifier and applying a second calculation rule to the second identifier for calculating a documentation value that defines a unique signature of each instance of a linking event between the first and second linking partners, wherein calculating the documentation value includes calculating a third identifier as a repetition value which uniquely represents a number of repetitions for a linking event between the first and second linking partners so repetitions of linking events can be documented in a distinguishable manner using a unique signature of the linking partners involved in the linking events;
  - causing synchronised storage of the calculated documentation value in memories of apparatuses of the network; and
  - safeguarding the operation of the apparatus for the first and second linking partners;
- an interface to a memory or with a memory for storing the calculated documentation value; and
- an interface to a network, via which the apparatuses exchange data.

13. The safeguarding module of claim 12, wherein the safeguarding module further comprises an interface to further safeguarding modules of other apparatuses of the network.

14. An apparatus comprising the safeguarding module of claim 12.

15. A system for safeguarding an apparatus in the medical environment against an unauthorised operation of the apparatus, the system comprising one or more computers and one or more computer storage media storing instructions that are operable, when executed by the one or more computers, to cause the one or more computers to perform operations comprises:
- reading-in a first identifier for identifying a first linking partner of the at least two linking partners in a unique manner and a second identifier for identifying a second linking partner of the at least two linking partners in a unique manner;
- applying at least a first calculation rule to the read-in first identifier and applying a second calculation rule to the second identifier for calculating a documentation value that defines a unique signature of each instance of a linking event between the first and second linking partners, wherein calculating the documentation value includes calculating a third identifier as a repetition value which uniquely represents a number of repetitions for a linking event between the first and second linking partners so repetitions of linking events can be documented in a distinguishable manner using a unique signature of the linking partners involved in the linking events;
- causing synchronised storage of the calculated documentation value in memories of apparatuses of the network; and
- safeguarding the operation of the apparatus for the first and second linking partners.

16. The system of claim 15, wherein the system includes multiple apparatuses, and memories of the apparatuses form a distributed memory structure.

17. The system of claim 15, wherein the first linking partner is a patient who is allocated the first identifier which identifies him and wherein the second linking partner is the medical item of use which is marked with an identification marking, wherein the second identifier is allocated in a unique manner to the identification marking, and wherein the linking event represents the use of the item of use for the patient during a treatment on a specific medical apparatus.

18. The system of claim 15, wherein the first linking partner is a membrane, wherein the membrane is designed having an identification marking which identifies it in a unique manner, wherein the first identifier is allocated in a unique manner to the identification marking, wherein the second linking partner is a reverse osmosis unit which is designed having an identification marking which identifies it in a unique manner and to which the second identifier is allocated in a unique manner, and wherein the linking event represents the use of the membrane in the reverse osmosis unit.

* * * * *